United States Patent
Martin et al.

(10) Patent No.: US 9,700,445 B2
(45) Date of Patent: Jul. 11, 2017

(54) ONE-WAY ACTUATOR KNOB

(71) Applicant: Abbott Cardiovascular Systems, Inc., Santa Clara, CA (US)

(72) Inventors: Jeffrey J. Martin, San Lorenzo, CA (US); Adrian M. Lim, Mountain View, CA (US); Tin Hoang, San Francisco, CA (US)

(73) Assignee: Abbott Cardiovascular Systems, Inc., Santa Clara, CA (US)

( * ) Notice: Subject to any disclaimer, the term of this patent is extended or adjusted under 35 U.S.C. 154(b) by 228 days.

(21) Appl. No.: 14/532,494

(22) Filed: Nov. 4, 2014

(65) Prior Publication Data

US 2016/0120672 A1 May 5, 2016

(51) Int. Cl.
*A61F 2/24* (2006.01)
*A61F 2/95* (2013.01)
(Continued)

(52) U.S. Cl.
CPC .............. *A61F 2/95* (2013.01); *A61B 17/122* (2013.01); *A61B 17/1285* (2013.01); *A61B 17/068* (2013.01); *A61B 17/128* (2013.01); *A61B 2017/00243* (2013.01); *A61B 2017/00292* (2013.01); *A61B 2017/00407* (2013.01); *A61B 2017/00623* (2013.01); *A61B 2017/00783* (2013.01); *A61B 2017/00845* (2013.01); *A61B 2017/00853* (2013.01); *A61B 2017/12054* (2013.01); *A61B 2017/12095* (2013.01); *A61F 2/2427* (2013.01); *A61F 2002/011* (2013.01); *A61F 2002/9505* (2013.01); *A61F 2002/9517* (2013.01)

(58) Field of Classification Search
CPC .... A61F 2/95; A61F 2/2427; A61F 2002/011; A61F 2002/9505; A61F 2002/9517; A61B 17/068; A61B 17/128; A61B 17/1285; A61B 2017/00243; A61B 2017/00292; A61B 2017/00367; A61B 2017/00407; A61B 2017/00623; A61B 2017/00783; A61B 2017/0647; A61B 2017/0648; A61B 2017/0649; A61B 2017/12054; A61B 2017/12095

See application file for complete search history.

(56) References Cited

U.S. PATENT DOCUMENTS

| 7,666,204 B2 * | 2/2010 | Thornton | A61B 50/30 606/148 |
| 2011/0208169 A1 | 8/2011 | Nash | |
| 2015/0272759 A1 * | 10/2015 | Argentine | A61F 2/966 623/1.11 |

FOREIGN PATENT DOCUMENTS

| WO | WO2011082350 | 7/2011 |
| WO | WO2012151543 | 11/2012 |

OTHER PUBLICATIONS

"FDA premarket approval—MitraClip Clip delivery system", Oct. 24, 2013, Retrieved from http://www.accessdata.fda.gov/cdrh_docs/pdf10/p100009a.pdf, Retrieved on Apr. 28, 2016, pp. 1-5.

(Continued)

*Primary Examiner* — Robert Lynch
(74) *Attorney, Agent, or Firm* — Workman Nydegger

(57) ABSTRACT

Embodiments of the present disclosure relate to apparatuses, systems, and methods for safely delivering and deploying an intravascular device. An apparatus for controlling an intravascular device may include a body having rotating assembly disposed through the body. The rotating assembly may be configured to hold a proximal end of an elongate mandrel. The rotating assembly may be rotationally connected to the body by a one-way bearing.

19 Claims, 9 Drawing Sheets

(51) Int. Cl.
*A61B 17/122* (2006.01)
*A61B 17/128* (2006.01)
*A61B 17/068* (2006.01)
*A61B 17/00* (2006.01)
*A61B 17/12* (2006.01)
*A61F 2/01* (2006.01)

(56) References Cited

OTHER PUBLICATIONS

"Diving watch", Sep. 25, 2014, Retrieved from https://en.wikipedia.org/w/index.php?title=Diving_watch&oldid=627082924, Retrieved on Apr. 28, 2016, Chapter: Elapsed time controller pp. 1-13.

Leitgeb, "Safety of Electromedical Devices: Law—Risks—Opportunities", May 6, 2010, Springer Science & Business Media ISBN: 978-3-211-99682-9, Retrieved from https://books.google.de, Retrieved on Apr. 28, 2016, pp. 66.

"MitraClip Clip Delivery System IFU Instructions for Use Mitraclip System Steerable Guide Catheter Ref No. SGC01ST Clip Delivery System Ref No. CDS02ST Mitraclip System Accessories Stabilizer Ref No. SZR01ST Lift Ref No. LFT01ST Support Plate Ref No. PLT01ST", Jan. 24, 2014, Retrieved from http://web.archive.org/web/*/http://www.fda.gov/downloads/AdvisoryCommittees/CommitteesMeetingMaterials/MedicalDevices/MedicalDevicesAdvisoryCommittee/CirculatorySystemDevicesPanel/UCM343688.pdf, Retrieved on Apr. 28, 2016, pp. 1-39.

\* cited by examiner

ONE-WAY ACTUATOR KNOB

CROSS-REFERENCE TO RELATED APPLICATIONS

N/A

BACKGROUND OF THE DISCLOSURE

1. The Field of the Invention

Generally, this disclosure relates to medical devices. Specifically, the present disclosure relates to intravascular devices. Even more specifically, present disclosure relates to the reliable control and deployment of intravascular devices.

2. Background and Relevant Art

Intravascular devices grant medical professionals the ability and option to perform healing procedures within a patient while avoiding more complicated, higher risk, and more expensive invasion procedures. The ability to access, for example, the heart through the femoral artery allows a medical profession to avoid open surgery and can save the patient days or weeks of recovery time. Open surgery carries with it potential complications. Open surgery can be take more time, require more personnel, lead to greater blood loss, and carry a greater infection risk during the procedure.

Additionally, the recovery period for open surgery carries significant downsides, as well. Any surgical opening requires time to healing upon closure. The healing time is longer for a larger opening. Larger openings may also carry with them a greater risk of infection during the healing process. The larger surface area that may become infection is an additional challenge, but the longer time period also creates problems as patients typically become less vigilant about maintaining the sterility and cleanliness of their sutures, staples, or other closures as time progresses.

Because intravascular procedures carry benefits over open surgery, they are used in increasing numbers. Intravascular procedures are also used to provide care to patients who may not be optimal candidates for open surgeries due to age or other medical concerns. Therefore, access to a variety of procedures is desirable. Consequentially, intravascular procedures may include the insertion and subsequent removal of intravascular devices or may include the placement of a device to remain in the patient's body, either temporarily or permanently. Both the incorrect or incomplete placement of an intravascular device, as well as the premature deployment of an intravascular device can cause significant complications. Incorrect, incomplete, or premature deployment may dictate a subsequent open surgery to retrieve or repair the intravascular device and even in a patient previously determined to be a non-ideal candidate for open surgery.

BRIEF SUMMARY

Embodiments of the present disclosure address one or more of the foregoing or other problems in the art with apparatuses, systems, and methods for more reliably controlling and deploying intravascular devices.

In a non-limiting embodiment, an apparatus for controlling an intravascular device includes a body containing a rotating assembly configured to hold an end of an elongated mandrel. The rotating assembly is rotationally connected to the body by a one-way bearing located between the rotating assembly and the body. The rotating assembly is rotated by an actuator knob. The one-way bearing allows the transmission of a rotational force from the rotating assembly to the elongate mandrel in one direction. The one-way bearing prevents the transmission of a rotational force from the body to the elongate mandrel in an opposite rotational direction.

In another non-limiting embodiment, a method of manufacture for an apparatus for controlling an intravascular device includes affixing an elongate mandrel within a rotating assembly. A one-way bearing is affixed inside a threaded insert. The threaded insert is threaded into a bore by applying torque in a locking direction of the one-way bearing. At least part of the rotating assembly is affixed within the one-way bearing.

In yet another non-limiting embodiment, an intravascular device delivery system includes an elongate mandrel with a proximal end and rotatable fastener at a distal end. An intravascular device is fastened to the rotatable fastener. The proximal end of the elongate mandrel is held by a rotating assembly in a controller. The controller includes a body in which the rotating assembly is located. An actuator knob is configured to rotate the rotating assembly relative to the body. The rotating assembly is connected to the body via a one-way bearing located between the rotating assembly and the body.

Additional features and advantages of embodiments of the disclosure will be set forth in the description which follows, and in part will be obvious from the description, or may be learned by the practice of such embodiments. The features and advantages of such embodiments may be realized and obtained by means of the instruments and combinations particularly pointed out in the appended claims. These and other features will become more fully apparent from the following description and appended claims, or may be learned by the practice of such embodiments as set forth hereinafter.

BRIEF DESCRIPTION OF THE DRAWINGS

In order to describe the manner in which the above-recited and other advantages and features of the disclosure can be obtained, a more particular description of the disclosure briefly described above will be rendered by reference to specific embodiments thereof which are illustrated in the appended drawings. For better understanding, the like elements have been designated by like reference numbers throughout the various accompanying figures. While some of the drawings are schematic representations, at least some of the figures may be drawn to scale. Understanding that these drawings depict only embodiments of the disclosure and are not therefore to be considered to be limiting of its scope, the disclosure will be described and explained with additional specificity and detail through the use of the accompanying drawings in which.

DETAILED DESCRIPTION

One or more embodiments of the present disclosure relate to controlling and deploying intravascular devices.

An intravascular device may be controlled and deployed by a controller operated by a medical profession outside the patient's vasculature. The controller may allow for the actuation of various components of the intravascular device and may allow the placement of the intravascular device. The placement of the device may include rotational and longitudinal placement in a vessel. Rotational placement may be effected by the translational of torque from the controller to the intravascular device. An elongate mandrel may connect the controller to the intravascular device and transmit longitudinal force and torque therebetween. The controller may include a rotatable actuator knob that may disconnect the intravascular device from the elongate mandrel.

The actuator knob may disconnect the intravascular device from the elongate mandrel when the actuator knob, and hence the elongate mandrel, is rotated in a counter clockwise direction. However, when rotated in the clockwise direction, the actuator knob, and hence the elongate mandrel, may damage the connection between the elongate mandrel and the intravascular device. A one-way bearing located between a body of the controller and a rotating assembly inside the controller may substantially limit the ability of the actuator knob to rotate in the clockwise direction and damage the connection between the elongate mandrel and the intravascular device. The one-way bearing may allow the rotation of the elongate mandrel without any perceivable interference to a user in a first direction. The one-way bearing may transmit torque from the actuator knob to the body of the controller, and hence the user's grip on the controller, when rotated in an opposite second direction. An incorrectly assembled controller may substantially inhibit counter clockwise rotation of the actuator knob and, hence, a medical professional's ability to disconnect and deploy an intravascular device. A method of manufacture is also presented herein to ensure correct directional assembly of a controller.

Figure 1:
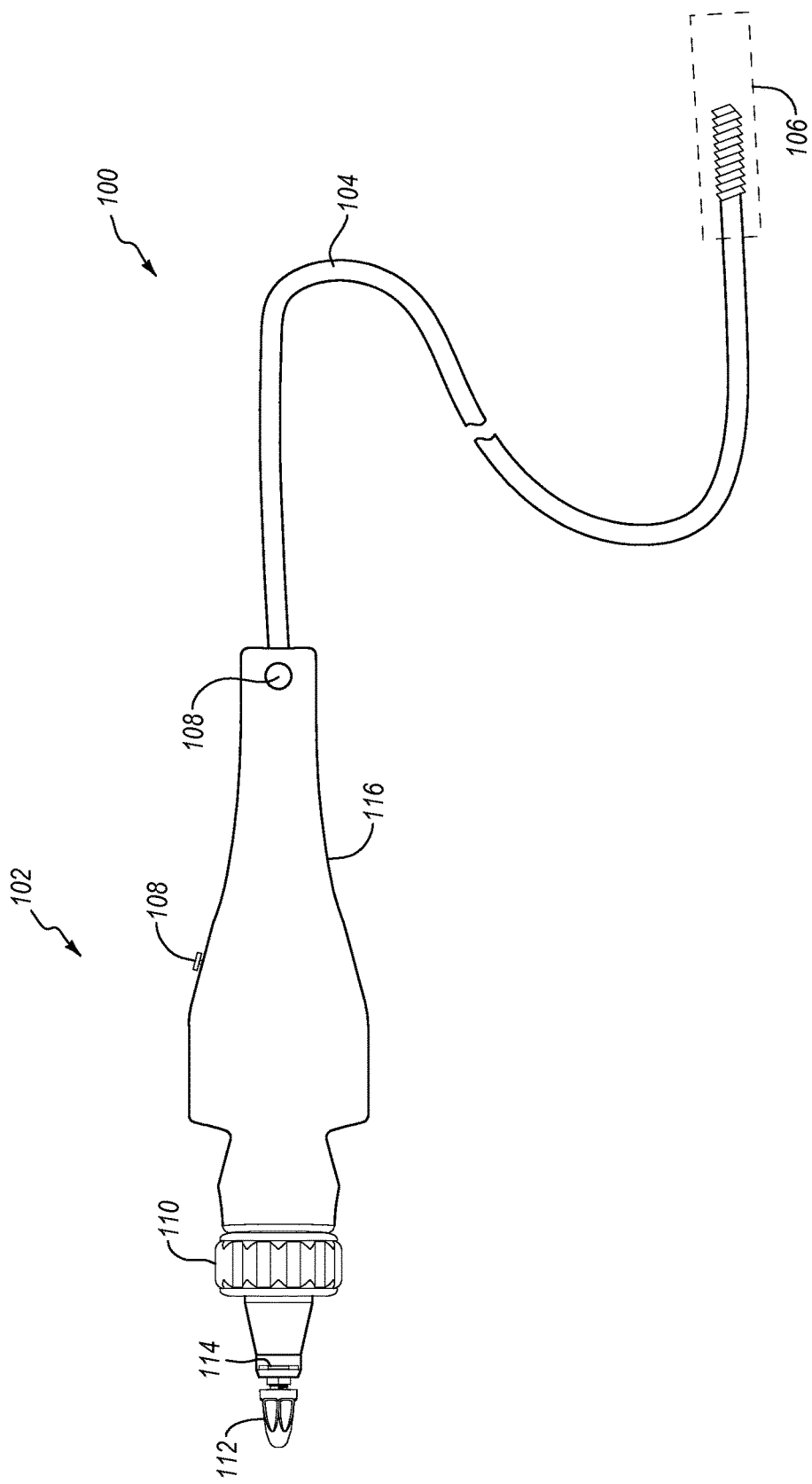
FIG. 1 illustrates an intravascular device delivery system according to the present disclosure.

FIG. 1 depicts an intravascular device delivery system 100 including a controller 102, an elongate mandrel 104, and an intravascular device 106. The controller 102 may be connected to a proximal end of the elongate mandrel 104 and the intravascular device 106 may be connected to a distal end of the elongate mandrel 104. The intravascular device 106 may include a variety of devices and is depicted schematically. In some embodiments, the intravascular device 106 may include a mitral valve repair device, such as a MITRACLIP available from Abbott Vascular. In other embodiments, the intravascular device 106 may include other vascular repair devices. In yet other embodiments, the intravascular device 106 may include filtration devices. In further embodiments, the intravascular device 106 may include pharmaceutical eluting devices. In some embodiments, the elongate mandrel 104 may connect to the intravascular device 106 by an internal threaded connection, an external threaded connection, a bayonet connection, other suitable rotational connection, or combinations thereof.

The elongate mandrel 104 may include a catheter, guidewire, other vascular sleeve, or combinations thereof. In some embodiments, the elongate mandrel 104 may have a working length less than about 1000 mm in length, greater than about 1000 mm in length, greater than about 1200 mm in length, or about 1220 mm in length. As used herein, "working length" should be understood to be the effective, usable length of a component or device during a medical procedure. For example, total length of the elongate mandrel 104 may be greater than the working length of the elongate mandrel 104 as portions of the elongate mandrel may be contained within other components, such as the intravascular device 106 or the controller 102.

The controller 102 is located at a distal end of the elongate mandrel 104. The controller 102 may include a variety of buttons 108 in order to control various functions or conditions of the intravascular device 106, pressure system (e.g. a bleedback valve) and/or a delivery mechanism. In the depicted embodiment, the controller 102 may include an arm positioner knob 110 for manipulating the arm positions of a mitral valve repair device. Actuator knob 112 is located at the proximal end of the controller 102. The rotation of the actuation knob 112 may be restricted by an actuator clip 114. The actuator clip 114 rotationally fixes a position of the actuator knob 112 relative to a controller body 116. The actuator clip 114 may be removed when rotation of the actuator knob 112, hence deployment of the intravascular device 106 is intended.

Figure 2:
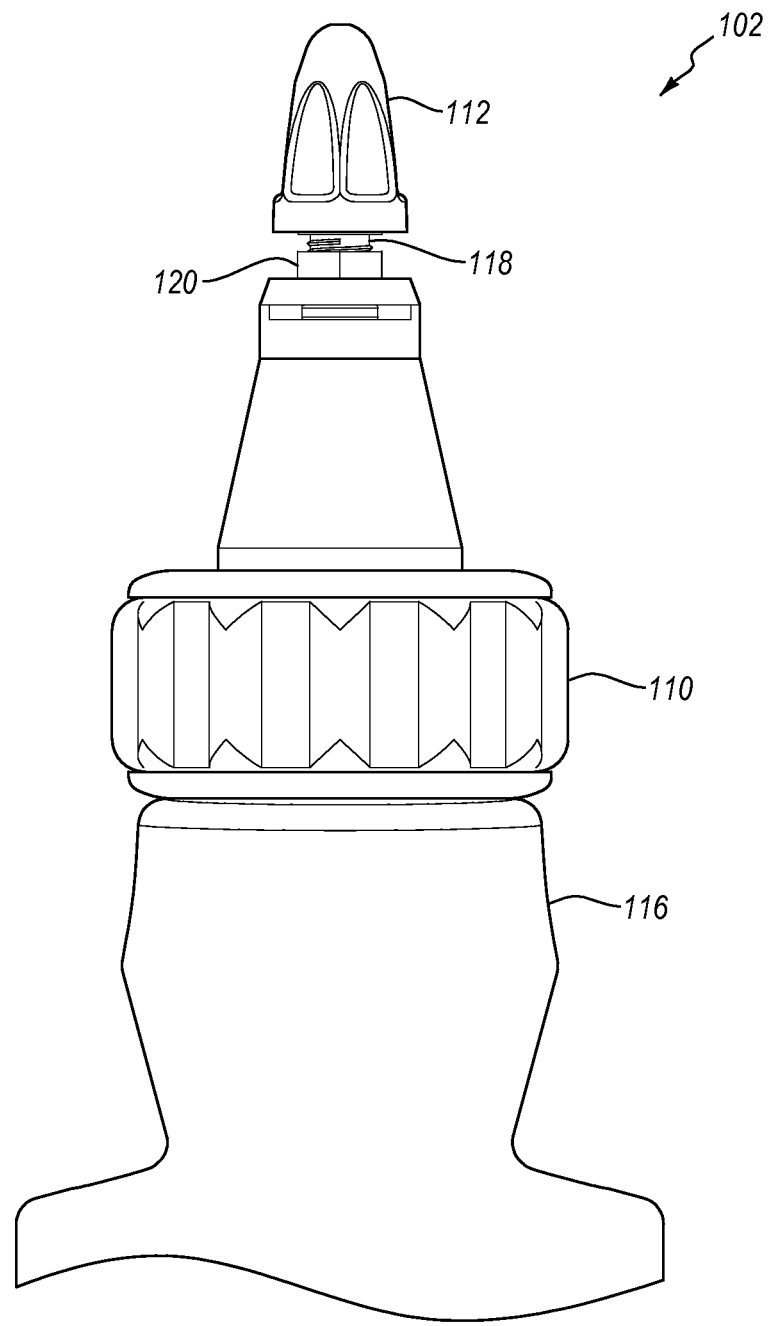
FIG. 2 illustrates a detail view of a controller including a one-way actuator knob.

FIG. 2 illustrates a detail view of the controller 102 and actuator knob 112 with the actuator clip 114 removed. The actuator knob 112 may be fixed to a threaded rod 118 that is inserted and threaded into a crimping cam 120 (visible in FIG. 3). The actuator knob 112 may thereby rotate the crimping cam 120 via torque transmitted by the threaded rod 118. The crimping cam 120 may rotate relative to the controller body 116 when the actuator clip 114 is removed from the crimping cam 120.

Figure 3:
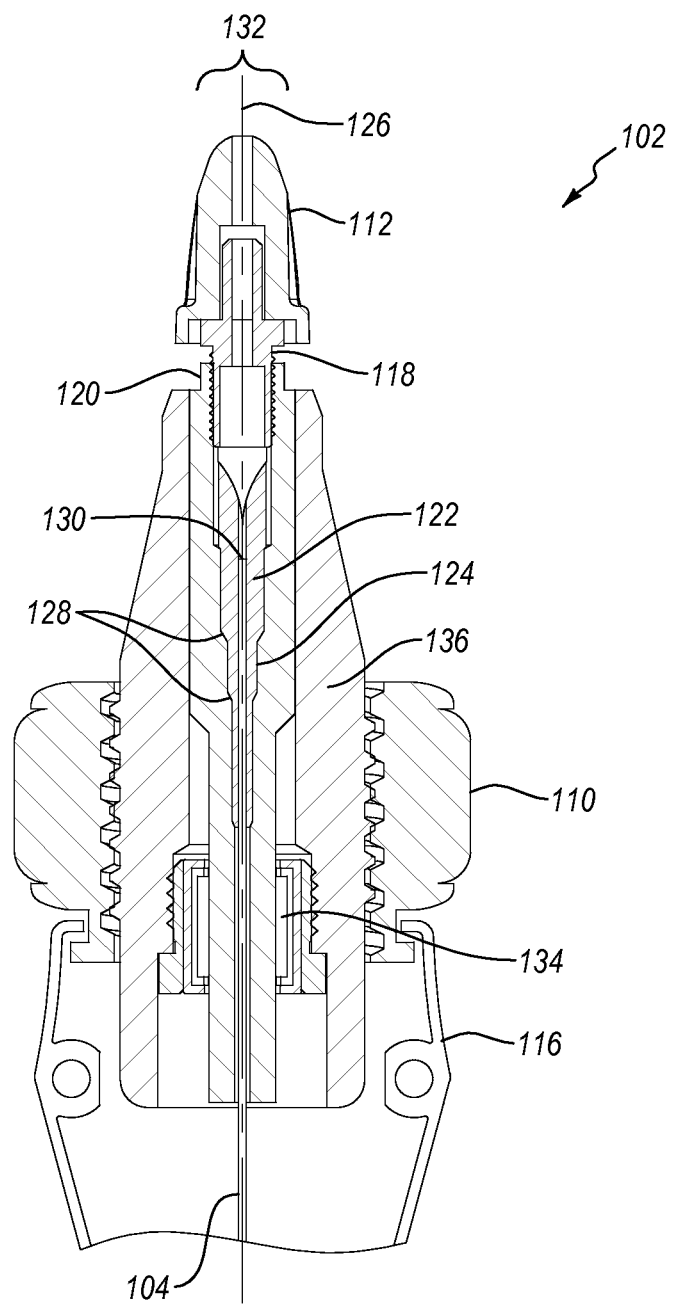
FIG. 3 illustrates a cross-sectional side view of a controller including a one-way actuator knob.

FIG. 3 shows a cross-sectional view of the controller 102 depicted in FIG. 2. As described, the actuator knob 112 may be fixed to a threaded rod 118, which is threaded into the crimping cam 120. The crimping cam 120 may include within it a collet 122. In some embodiments, the crimping cam 120 may be generally cylindrical, for example, having a circular transverse cross-section. In other embodiments, the interior surface 124 of the crimping cam 120 may have a polygonal transverse cross-section such a square, a pentagon, a hexagon, and similar or an irregular polygon. Similarly, in some embodiments, the collet 122 may be generally cylindrical and have a circular transverse cross-section. In other embodiments, the collet 122 may have a polygonal transverse cross-section such a square, a pentagon, a hexagon, and similar or an irregular polygon. In some embodiments, the collet 122 may mate complimentarily with an interior surface 124 of the crimping cam 120.

The actuator knob 112, threaded rod 118, crimping cam 120, collet 122 may share a longitudinal axis 126 about which they may all rotate. As such, the shared longitudinal axis 126 may also be a shared rotational axis. The threaded rod 118 may apply a longitudinal compression force upon the collet 122 as the threaded rod 118 is rotated against the complimentarily threaded crimping cam 120. The compression force on the collet 122 may cause the collet to move longitudinally and strike one or more tapers 128 on the crimping cam 120. The tapers 128 may apply a lateral compression force upon the collet 122. The lateral compression force may, in turn, cause the collet 122 to impinge upon a proximal end 130 of the elongate mandrel 104.

The collet 122 may thereby hold the proximal end 130 of the elongate mandrel 104 in within the rotating assembly 132. The rotating assembly 132 may include the actuator knob 112, threaded rod 118, collet 122, and crimping cam 120. The rotating assembly 132 may rotate relative to the controller body 116. In some embodiments, the rotating assembly 132 may rotate upon a one-way bearing 134 located between the rotating assembly 132 and an actuator slider 136. The actuator slider 136 may be rotationally fixed relative to the controller body 116. In other embodiments, the rotating assembly 132 may rotate upon a one-way bearing 134 located between the rotating assembly 132 and the controller body 116.

In some embodiments, the one-way bearing 134 may be a rotational clutch bearing. In other embodiments, the one-way bearing 134 may be a ratcheting bearing. In an embodiment, the one-way bearing 134 may be an annular or cylindrical rotational bearing. The rotating assembly 132 may be rotationally fixed relative an inner surface of the one-way bearing. In various embodiments, the rotating assembly 132 and one-way bearing 134 are fixed using a friction fit, a press fit, an adhesive, a weld, other suitable attachment mechanism, or combinations thereof. A clutch bearing may freely enable rotation of the rotating assembly 132 in a first direction while allowing for nearly instant resistance to be applied when rotated in a second direction. Similarly, a ratcheting bearing may allow freely enable rotation in the first direction, but may allow some degree of backlash in the second direction. As used herein, "rotating direction" should be understood to refer to the rotational direction in which the one-way bearing 134 rotates with relatively little friction. "Locking direction" should be understood to refer to the rotational direction in which the one-way bearing 134 may resist rotation and transfer torque. The ratcheting bearing may result in a tactile "clicking" sensation during operation. In some environments, such a sensation may be undesirable due to medical professional's experience and training with other rotation systems. When changing from a rotation system such as a bi-direction actuator having a rotating inner component and stationary outer component separated only by a simple bearing surface, the change from a simple bearing surface with near constant friction to a ratcheting system may result in a foreign tactile sensation. In at least some embodiments therefore, it may be desirable to retain as much familiar tactile performance as possible to encourage adoption of embodiments incorporating a one-way bearing 134.

Figure 4:
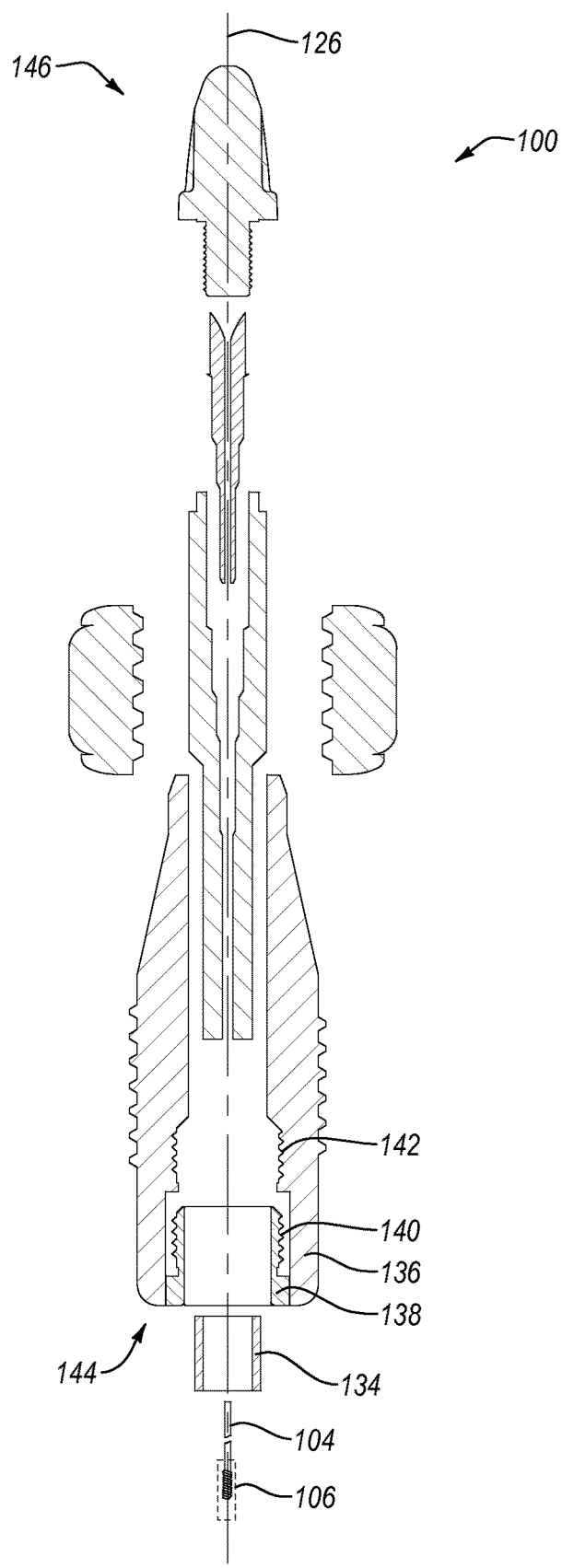
FIG. 4 illustrates an exploded cross-sectional side view of an actuator slider and one-way actuator knob.

The one-way bearing 134 may rotate freely in the "rotating direction" and "lock" when torque is applied in the "locking direction." To help ensure the one-way bearing 134 is installed in the controller 102 in the proper orientation, a number of indicators and design structures may be employed. In an embodiment, the one-way bearing may have a visual indicator imprinted, embossed, and/or applied to a surface indicating the rotating direction. In another embodiment, the locking direction may be leveraged during the assembly process. FIG. 4 depicts a controller 102 expanded along the longitudinal axis 126. In some embodiments, the one-way bearing 134 is connected to the interior of a threaded insert 138. In other embodiments, the one-way bearing 134 may have threads integrated into the one-way bearing 134, itself. The one-way bearing 134 may be connected to the interior of a threaded insert 138 by a friction fit, a press fit, an adhesive, a weld, other suitable attachment mechanism, or combinations thereof.

The threaded insert 138 may use the locking direction of the affixed one-way bearing 134 to drive the threaded insert 138 into the actuator slider 136. The threaded insert 138 may include left-hand threads 140 (opposite of the common threading direction) on a lateral surface thereof, which may mate with complimentary threads 142 on the actuator slider 136. The locking direction of the one-way bearing 134 may therefore transfer torque to the threaded insert 138 when the one-way bearing 134 is aligned such that the locking direction is oriented in the direction of the left-hand threads 140. The rotating direction of the one-way bearing 134 may also substantially prevent the transfer of torque to the threaded insert 138 when the one-way bearing 134 is aligned such that the rotating direction is oriented in the direction of the left-hand threads 140.

The threaded insert 138 may be driven into the actuator slider 136 therefore when the locking direction of the one-way bearing 134 is oriented counter-clockwise when viewed from a distal end 144 of the controller 102. When viewed from a proximal end 146 of the controller 102, the locking direction of the one-way bearing 134 may be the clockwise direction. Accordingly, the rotating direction of the one-way bearing 134 may permit rotation in the counter-clockwise direction when viewed from the proximal end 146 of the controller 102. As an operator will view the controller 102 from the proximal end 146, the one-way bearing 134 may allow rotation of the actuator knob 112, and hence rotating assembly 132 and elongate mandrel 104 in a counter-clockwise direction. The counter-clockwise rotation of the elongate mandrel 104 may disconnect and/or deploy the intravascular device 106 at the distal end of the elongate mandrel 104.

Figure 5:
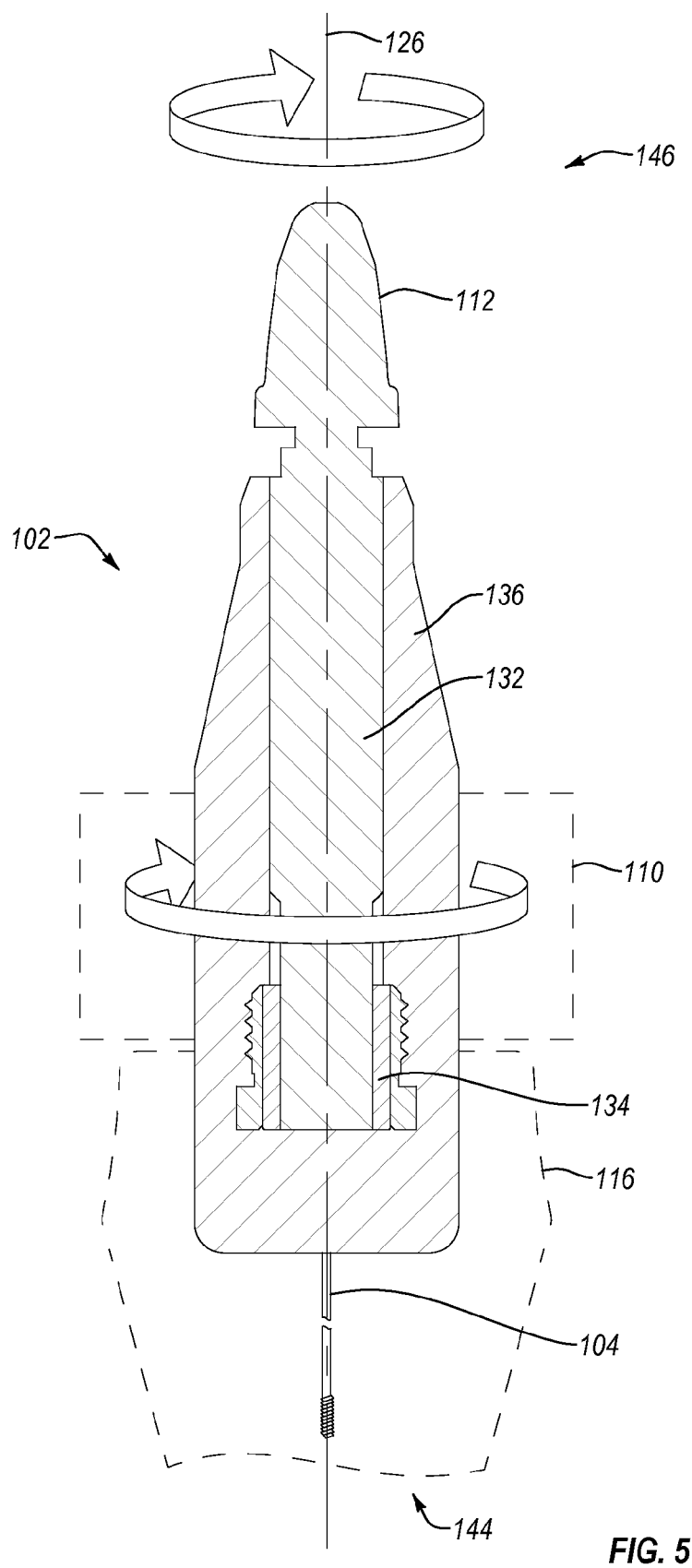
FIG. 5 schematically illustrates a one-way actuator knob transferring torque to the body of the controller.

As shown in FIG. 5, applying torque to the actuator knob 112 may apply a torque to the rotating assembly 132. When the torque vector is in the distal direction (according to the right-hand rule) toward the distal end 144 of the controller 102, the one-way bearing 134 may transmit the torque to act upon the actuator slider 136. The actuator slider 136 may be rotationally fixed to the controller body 116. The controller body 116 may be held by a user during operation of the actuator knob 112. The actuator knob 112 may have a smaller radius than the controller body 116. Therefore, the user may use comparatively little force to hold the controller body 116 still during the transmission of torque from the actuator knob 112 to the controller body 116. This may effectively prevent substantial movement of the controller 102 during application of torque to the actuator knob 112 in the locking direction.

Figure 6:
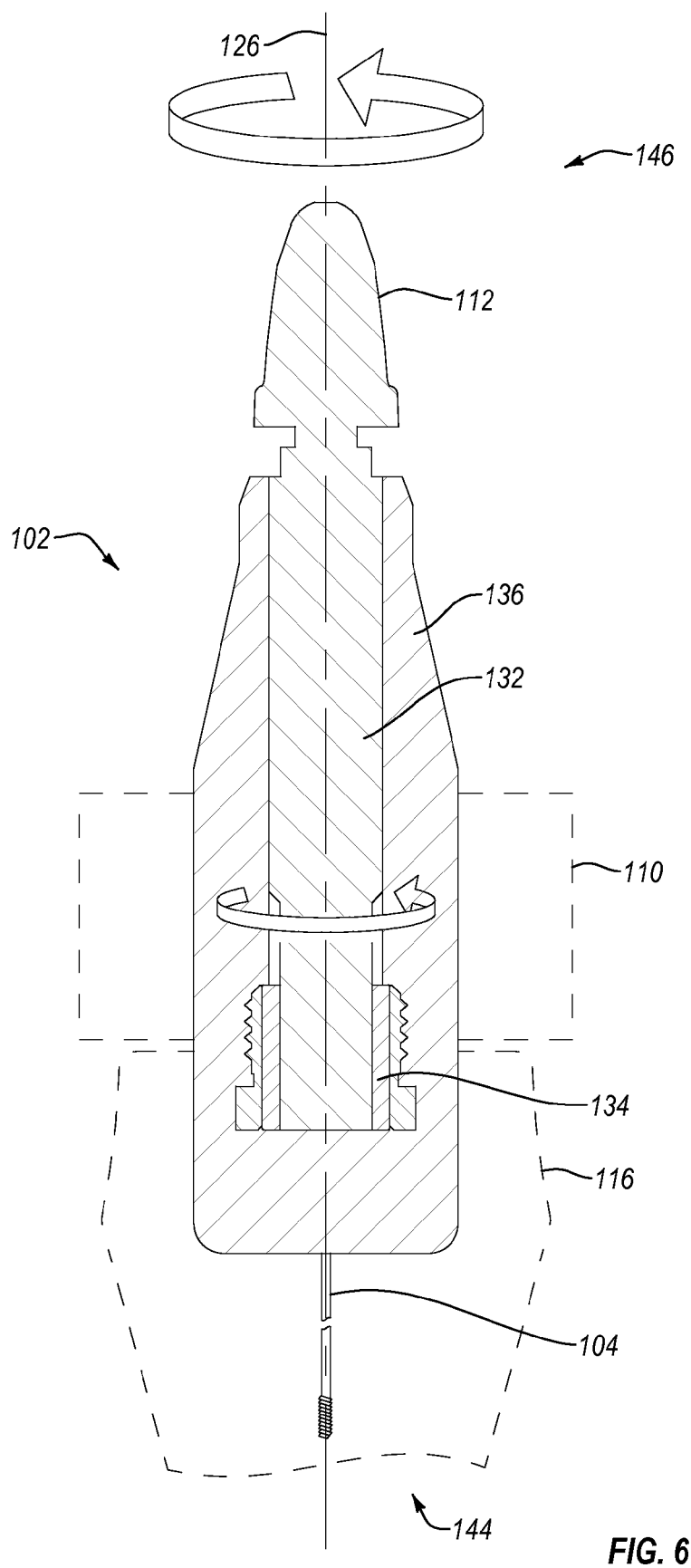
FIG. 6 schematically illustrates a one-way actuator knob allowing rotation of the knob without transferring torque to the body of the controller.

As shown in FIG. 6, applying torque to the actuator knob 112 toward the proximal end 146 (according to the right-hand rule) may apply torque to the rotating assembly 132. The one-way bearing 134 may transmit little to no torque to the controller body 116 through the threaded insert 138, thereby allowing rotation of the rotating assembly 132 about the longitudinal axis 126. The rotation of the rotating assembly 132 about the longitudinal axis may rotate the elongate mandrel 104.

The rotating assembly 132 may be connected via the one-way bearing to the controller body 116 directly or via the actuator slider 136. The rotating assembly 132 may be "held" in place when the one-way bearing 134 transfers torque to the actuator slider 136, which may be, in turn, held in place by the body 116. An operator may then resist the rotation of the body manually. The rotating assembly 132 may also be connected to the controller body 116 directly via the one-way bearing 134, such that the one-way bearing 134 transfers torque directly from the rotating assembly 132 to the controller body 116.

Figure 7:
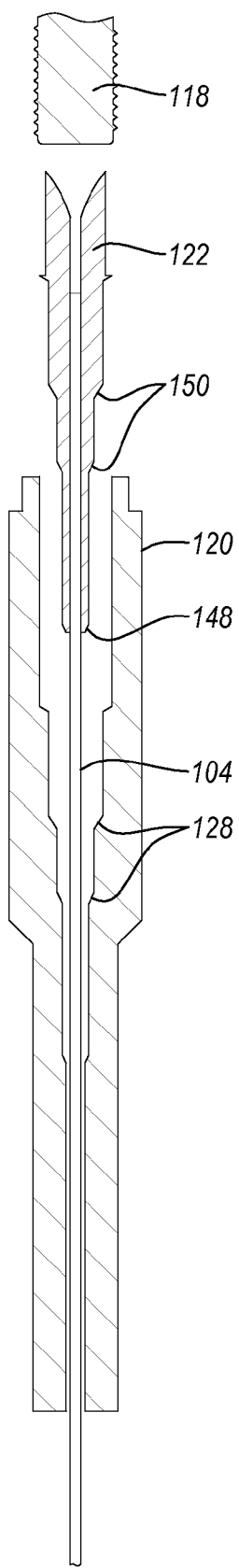
FIG. 7 illustrates a cross-sectional side view of a rotating assembly.

As described in relation to FIG. 3, the intravascular device delivery system 100 of the present disclosure may use the mechanical characteristics of some components during a manufacturing process. As shown in FIG. 7, the assembly of an intravascular device delivery system 100 may include the assembly of a controller 102. The elongate mandrel 104 may be inserted into the collet 122. The elongate mandrel 104 may extend from a tapered end 148 of the collet 122 and the proximal end 130 of the elongate mandrel 104 may be within the collet 122. The collet 122 may be inserted into the crimping cam 120. In an embodiment, the crimping cam 120 may include one or more tapers 128 that compliment tapers 150 on the collet 122. In other embodiments, the crimping cam 120 may include one or more tapers 128 that do not compliment tapers 150 on the collet 122. The crimping cam 120 may have a decreasing inner radius that applies a compressive force to the collet 122 as the collet 122 moves proximally within the crimping cam 120. While FIG. 7 depicts an embodiment of a crimping cam 120 having tapers 150, the depicted profile should be understood to be a non-limiting example of a crimping cam design.

The collet 122 may be retained within the crimping cam 120 by the threaded rod 118. When threaded through the complimentary threads on the crimping cam 120, the threaded rod 118 may apply a longitudinal compressive force on the collet 122. The crimping cam 120, collet 122, actuator knob 112, and threaded rod 118 form the rotating assembly 132 and define the rotational component within the actuator slider 136 and the controller body 116.

Figure 8:
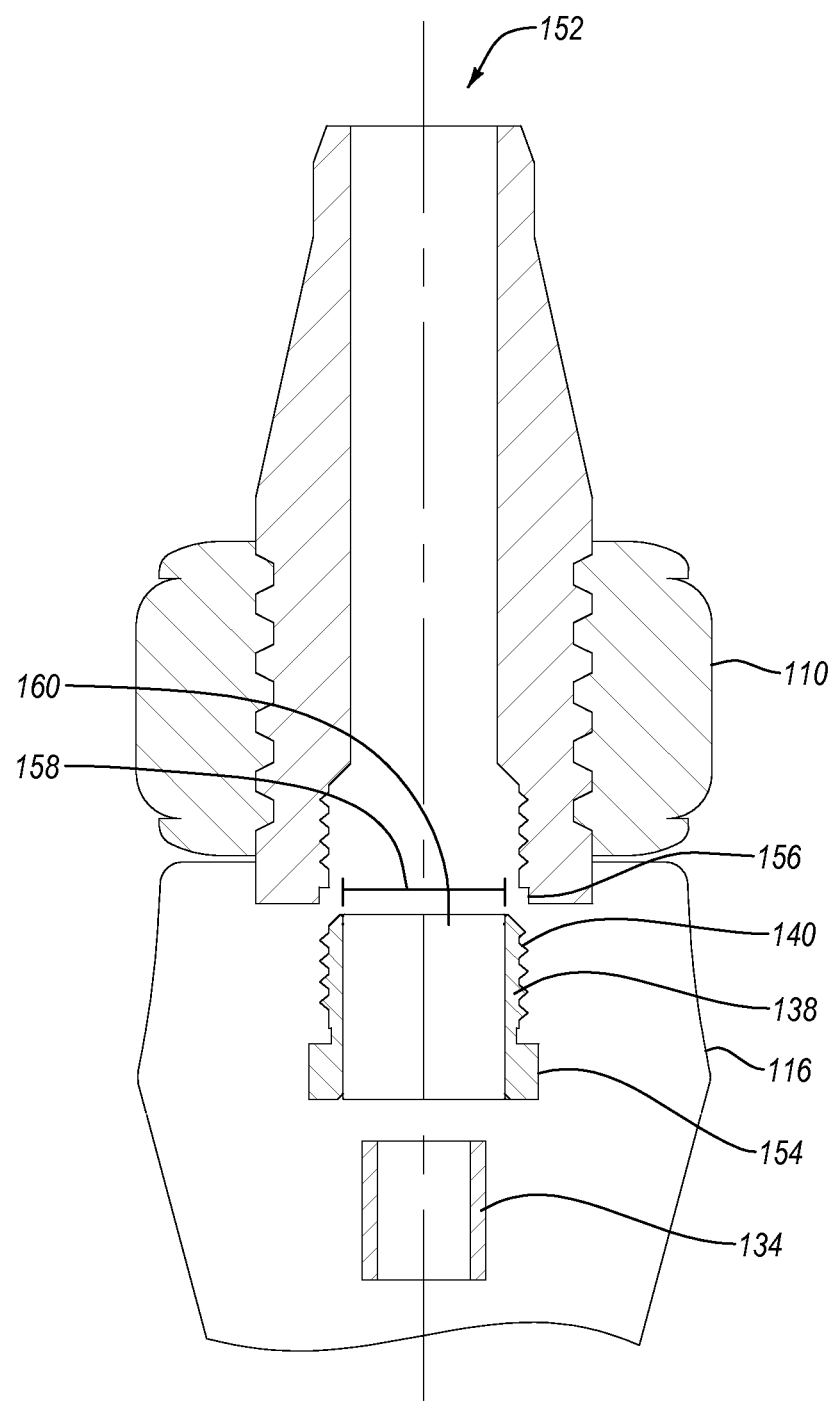
FIG. 8 illustrates the mounting of a one-way bearing in a controller.

FIG. 8 depicts the assembly of the controller body 116, actuator slider 136, threaded insert 138, and one-way bearing 134. In an embodiment, the assembly process may include attaching the one-way bearing 134 to the interior of the threaded insert 138. The one-way bearing 134 may include indicia (not shown) that indicate the rotating direction and locking direction. In some embodiments, the threaded insert 138 may include a slight taper on the interior diameter 158 such that the one-way bearing 134 may be inserted into the threaded insert from the proximal end of the threaded insert 160 (the end opposing the flange 154) such that the one-way bearing 134 can only be inserted into the threaded insert 138 before the threaded insert 138 is inserted into the actuator slider 136. The threaded insert 138 may include left-hand threads 140 and a flange 154 that complimentarily mate with the complimentary threads 142 and a notch 156 on the actuator slider 136. The threaded insert 138 may, therefore, fit in the actuator slider 136 in one direction. The threaded insert 138 may then be driven into the actuator slider 136 along the left-hand threads 140 and complimentary threads 142 by applying torque to the one-way bearing 134 and rotating the one-way bearing 134 in the locking direction.

If the one-way bearing 134 is oriented correctly in the threaded insert 138, and the threaded insert 138 is aligned correctly with the actuator slider 136, the threaded insert 138 will drive into the actuator slider 136 and affix the one-way bearing 134 to the actuator slider 136 in the desired orientation. If the one-way bearing 134 is oriented incorrectly in the threaded insert 138, the application of torque to the one-way bearing 134 will result in the one-way bearing 134 rotating in the rotating direction and fail to transfer any torque to drive the threaded insert 138 into the actuator slider 136. The actuator slider 136 may have a bore 152 extending therethrough, into which the rotating assembly 132 may fit.

Figure 9:
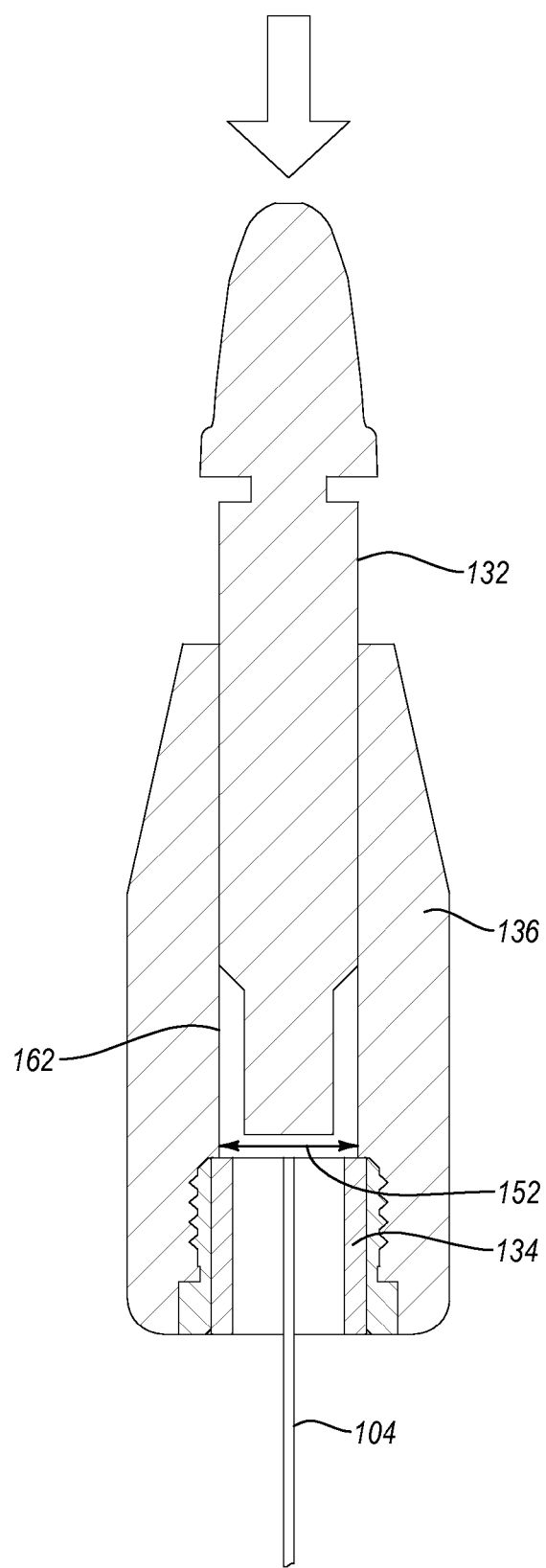
FIG. 9 illustrates the assembly of a controller according to the present disclosure.

FIG. 9 shows a schematic representation of the rotating assembly 132 being inserted into the one-way bearing 134 that has been affixed to the actuator slider 136 according to the method described in relation to FIG. 8. The rotating assembly 132 may be connected to the interior of the one-way bearing 134 using a friction fit, a press fit, an adhesive, a weld, other suitable attachment mechanism, or combinations thereof, as described in relation to FIG. 3. The rotating assembly 132 may be contained within a bore 152 that extends through the actuator slider 136. The rotating assembly 132 may contact the wall of the bore 152. In an embodiment, the controller 102 may include a layer of boundary material 162 between the rotating assembly 132 and the wall of the bore 152.

In some embodiments, the boundary material 162 may be made of or include a low-friction and/or lubricious material. For example, the the boundary material 162 may be made of or include polyoxymethylene, polytetraflouroethylene, or similar materials. In other embodiments, the boundary material 162 may be a low-wear, high durability coating. In some embodiments, the boundary material 162 may include a coating on the rotating assembly 132, a coating on the wall of the bore 152, integral to the rotating assembly 132, integral to the wall of the bore 152, or combinations thereof. Additionally, the boundary material 162 may be a discrete component providing a substantially circumferential boundary around the rotating assembly 132. In an embodiment, the boundary material 162 may be a continuous layer. For example, the boundary material 162 may cover the entirety of the surface, longitudinally and/or circumferentially around the rotating assembly 132. In another embodiment, the boundary material 162 may include a non-continuous and/or intermittent distribution that provides a set space between the rotating assembly 132 and the wall of the bore 152. For example, the boundary material 162 may include a plurality of circumferential strips that are spaced along the longitudinal length of the rotating assembly 132. In another example, the boundary material 162 may include a plurality of longitudinal strips that are spaced along the circumference of the rotating assembly 132.

The terms "approximately," "about," and "substantially" as used herein represent an amount close to the stated amount that still performs a desired function or achieves a desired result. For example, the terms "approximately," "about," and "substantially" may refer to an amount that is within less than 10% of, within less than 5% of, within less than 1% of, within less than 0.1% of, and within less than 0.01% of a stated amount.

In the description herein, various relational terms are provided to facilitate an understanding of various aspects of some embodiments of the present disclosure. Relational terms such as "bottom," "below," "top," "above," "back," "front," "left," "right," "rear," "forward," "up," "down," "horizontal," "vertical," "clockwise," "counterclockwise," "upper," "lower," and the like, may be used to describe various components, including their operation and/or illustrated position relative to one or more other components. For example, "proximal" and "distal" may indicate position and direction relative to the operator during use of the intravascular delivery system. Relational terms do not indicate a particular orientation for each embodiment within the scope of the description or claims. Accordingly, relational descriptions are intended solely for convenience in facilitating reference to various components, but such relational aspects may be reversed, flipped, rotated, moved in space, placed in a diagonal orientation or position, placed horizontally or vertically, or similarly modified unless otherwise specified. Certain descriptions or designations of components as "first," "second," "third," and the like may also be used to differentiate between identical components or between components which are similar in use, structure, or operation. Such language is not intended to limit a component to a singular designation. As such, a component referenced in the specification as the "first" component may be the same or different than a component that is referenced in the claims as a "first" component.

Furthermore, while the description or claims may refer to "an additional" or "other" element, feature, aspect, component, or the like, it does not preclude there being a single element, or more than one, of the additional element. Where the claims or description refer to "a" or "an" element, such reference is not be construed that there is just one of that element, but is instead to be inclusive of other components and understood as "at least one" of the element. It is to be understood that where the specification states that a component, feature, structure, function, or characteristic "may," "might," "can," or "could" be included, that particular component, feature, structure, or characteristic is provided in some embodiments, but is optional for other embodiments of the present disclosure. The terms "couple," "coupled," "connect," "connection," "connected," "in connection with," and "connecting" refer to "in direct connection with," or "in connection with via one or more intermediate elements or members." Components that are "integral" or "integrally" formed include components made from the same piece of material, or sets of materials, such as by being commonly molded or cast from the same material, or commonly machined from the same piece of material stock. Components that are "integral" should also be understood to be "coupled" together.

Although various example embodiments have been described in detail herein, those skilled in the art will readily appreciate in view of the present disclosure that many modifications are possible in the example embodiments without materially departing from the present disclosure. Accordingly, any such modifications are intended to be included in the scope of this disclosure. Likewise, while the disclosure herein contains many specifics, these specifics should not be construed as limiting the scope of the disclosure or of any of the appended claims, but merely as providing information pertinent to one or more specific embodiments that may fall within the scope of the disclosure and the appended claims. Any described features or elements from the various embodiments disclosed may be employed in combination with any other features or elements disclosed herein.

A person having ordinary skill in the art should realize in view of the present disclosure that equivalent constructions do not depart from the spirit and scope of the present disclosure, and that various changes, substitutions, and alterations may be made to embodiments disclosed herein without departing from the spirit and scope of the present disclosure. Equivalent constructions, including functional "means-plus-function" clauses are intended to cover the structures described herein as performing the recited function, including both structural equivalents that operate in the same manner, and equivalent structures that provide the same function. It is the express intention of the applicant not to invoke means-plus-function or other functional claiming for any claim except for those in which the words 'means for' appear together with an associated function. Each addition, deletion, and modification to the embodiments that falls within the meaning and scope of the claims is to be embraced by the claims.

What is claimed is:

1. An apparatus for controlling an intravascular device, the apparatus comprising:
    a body;
    an elongate mandrel having a proximal end and a distal end, the elongate mandrel have a rotatable fastener at the distal end, the rotatable fastener selectively coupled to the intravascular device;
    a rotating assembly configured to hold the proximal end of the elongate mandrel, the rotating assembly being disposed within the body;
    an actuator knob configured to rotate the rotating assembly; and
    a one-way bearing disposed circumferentially between at least part of the rotating assembly and the body, and within a threaded insert disposed within the body, that allows transmission of a first rotational force from the rotating assembly to the elongate mandrel in one rotational direction to release the intravascular device from coupling with the elongate mandrel, while preventing the transmission of a second rotational force from the body to the elongate mandrel in an opposite rotational direction, the distal end of the elongate mandrel being disposed distal a distal end of the threaded insert.

2. The apparatus of claim 1, wherein the threaded insert has left-hand threads.

3. The apparatus of claim 1, wherein the one-way bearing is a clutch bearing.

4. The apparatus of claim 1, further comprising a locking pin configured to rotationally fix the rotating assembly relative to the body.

5. The apparatus of claim 1, wherein the rotating assembly is configured to hold the proximal end of the elongate mandrel using a collet.

6. The apparatus of claim 1, wherein the one-way bearing is configured to transfer torque from the rotating assembly to the body when the torque has a vector substantially oriented towards the distal end of the elongate mandrel.

7. A method of manufacture for an apparatus for controlling an intravascular device, the method comprising:
    affixing an elongate mandrel within a rotating assembly, the elongate mandrel having a distal end and a proximal end;
    affixing a one-way bearing within a threaded insert, the one-way bearing having a rotating direction and a locking direction;
    threading the threaded insert into a bore, the threaded insert being driven into the bore by applying a torque to the one-way bearing in the locking direction; and
    affixing at least part of the rotating assembly within the one-way bearing.

8. The method of claim 7, wherein the threaded insert includes left-hand threads.

9. The method of claim 7, wherein the threaded insert comprises a tapered inner diameter configured to receive the one-way bearing in a press fit from only one direction.

10. The method of claim 7, wherein affixing an elongate mandrel within a rotating assembly includes compressing the elongate mandrel within a collet.

11. The method of claim 7, further comprising connecting an intravascular device to the distal end of the elongate mandrel using a rotatable fastener.

12. The method of claim 7, wherein affixing a one-way bearing within a threaded insert includes press fitting the one-way bearing within the threaded insert.

13. The method of claim 7, wherein threading the threaded insert into a bore further comprises aligning a flange on the threaded insert with a notch at an end of the bore.

14. An intravascular device delivery system, the system comprising:
    an elongate mandrel having a proximal end and a distal end;

an intravascular device fastened to the distal end; and a controller having a body, a rotating assembly configured to hold the proximal end of the elongate mandrel, the rotating assembly disposed within the body, an actuator knob configured to rotate a portion of the rotating assembly, a threaded insert disposed within the body, and a one-way bearing disposed circumferentially between at least part of the rotating assembly and the body and within the threaded insert, the distal end of the elongate mandrel being disposed distal a distal end of the threaded insert.

15. The system of claim 14, wherein the one-way bearing is a clutch bearing.

16. The system of claim 14, wherein the intravascular device is a mitral valve repair device.

17. The system of claim 14, wherein the threaded insert is fixed relative to the body.

18. The system of claim 17, wherein the threaded insert comprises a left hand thread.

19. The system of claim 17, wherein the threaded insert comprises a flange.

* * * * *